US010384208B2

(12) United States Patent
Tan et al.

(10) Patent No.: US 10,384,208 B2
(45) Date of Patent: Aug. 20, 2019

(54) SYSTEMS AND METHODS FOR A THERMAL CYCLER HEATED COVER

(71) Applicant: LIFE TECHNOLOGIES CORPORATION, Carlsbad, CA (US)

(72) Inventors: Zeqi Tan, Singapore (SG); Wuh Ken Loh, Singapore (SG); Siew Yin Lee, Singapore (SG); Kuan Moon (Bernard) Boo, Singapore (SG)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 33 days.

(21) Appl. No.: 15/387,631

(22) Filed: Dec. 21, 2016

(65) Prior Publication Data

US 2017/0173587 A1    Jun. 22, 2017

Related U.S. Application Data

(60) Provisional application No. 62/270,695, filed on Dec. 22, 2015.

(51) Int. Cl.
| C12M 1/38 | (2006.01) |
| B01L 7/00 | (2006.01) |
| G01N 35/02 | (2006.01) |

(52) U.S. Cl.
CPC .............. *B01L 7/52* (2013.01); *G01N 35/026* (2013.01); *B01L 2200/025* (2013.01);
(Continued)

(58) Field of Classification Search
CPC ........ B01L 3/50851; B01L 7/52; B01L 9/523; B01L 2200/025; B01L 2200/04;
(Continued)

(56) References Cited

U.S. PATENT DOCUMENTS 6,197,572 B1 *  3/2001  Schneebeli ......... B01L 3/50851
                                                        435/286.2
2004/0112969 A1    6/2004  Saga et al.
(Continued)

FOREIGN PATENT DOCUMENTS

EP          0955097       11/1999

OTHER PUBLICATIONS

PCT/US2016/068154, "International Search Report dated", Mar. 13, 2017, 5 Pages.

*Primary Examiner* — William H. Beisner
(74) *Attorney, Agent, or Firm* — Jones Robb, P.L.L.C.

(57) ABSTRACT

A thermal cycler system for use with a sample holder configured to receive a plurality of samples includes a sample block configured to receive the sample holder, a cover lid configured to move in a direction toward the sample block from an open position to a closed position, a heated cover operatively coupled to the cover lid and configured to move in a direction toward the sample block from a raised position to a first lowered position, in which the heated cover contacts the sample holder when the sample holder is received by the sample block, and a drive assembly including a motion guide configured to move in a direction toward the sample block from a first position, wherein the cover lid is in the open position and the heated cover is in the raised position, to a second position, wherein the cover lid is in the closed position.

24 Claims, 11 Drawing Sheets

(52) U.S. Cl.
CPC ... *B01L 2200/143* (2013.01); *B01L 2300/041* (2013.01); *B01L 2300/045* (2013.01); *B01L 2300/046* (2013.01); *B01L 2300/0609* (2013.01); *B01L 2300/0663* (2013.01); *B01L 2300/18* (2013.01); *B01L 2300/1827* (2013.01)

(58) Field of Classification Search
CPC ..... B01L 2300/0609; B01L 2300/0829; B01L 2300/0858
See application file for complete search history.

(56) References Cited

U.S. PATENT DOCUMENTS

2005/0282270 A1    12/2005    Shin et al.
2012/0279954 A1    11/2012    Ceremony et al.

\* cited by examiner

SYSTEMS AND METHODS FOR A THERMAL CYCLER HEATED COVER

CROSS REFERENCE TO RELATED APPLICATIONS

This application claims the benefit under 35 U.S.C. § 119(e) of U.S. Provisional Patent Application No. 62/270,695 filed on Dec. 22, 2015. The entire contents of the aforementioned applications are incorporated by reference herein.

TECHNICAL FIELD

The present invention relates generally to thermal cycler systems and methods of using same.

BACKGROUND

Testing of biological or chemical samples often requires a device for repeatedly subjecting multiple samples though a series of temperature cycles. To prepare, observe, test, and/or analyze an array of biological samples, one example of an instrument that may be utilized is a thermal cycler or thermocycling device, such as an end-point polymerase chain reaction (PCR) instrument or a quantitative, or real-time, PCR instrument. Such devices are used to generate specific temperature cycles, i.e. to set predetermined temperatures in the reaction vessels to be maintained for pre-determined intervals of time.

Generally, it is desirable to increase the efficiency and output of the PCR process. Advances in automated biological sample processing instruments allow for quicker and more efficient analysis of samples. However, such automated systems often must be capable of integrating with other automated laboratory systems. Eliminating user interaction increases efficiency but requires the development of feedback controls to cue the main instrument controller that the next stage in the process is ready to occur. For example, the system must be sure that a sample holder is in place within the biological analysis system before activating the thermal cycling routine. In an automated system where there are no user interventions, it is desirable to cue the main instrument controller that the sample holder is in place based on feedback by the lab automation system.

A potential method to detect that the consumer plate in position is the use of an imaging system integrated into the main lab automation system. The imaging system may capture an image and, through complex algorithms, determine the presence of a sample holder on the sample block of the PCR system. Such a method is complex, costly, and tedious to implement. Other methods include the embedding of a sensitive load cell on the sample block module or the use of a barcode reader, which can detect the presence of the plate through a weight change or a barcode on the sample holder, respectively. However, such methods are costly to implement.

There is an increasing need to provide improved thermal cycler systems that address one or more of the above drawbacks.

SUMMARY

In accordance with one embodiment, a thermal cycler system for use with a sample holder configured to receive a plurality of samples includes a sample block configured to receive the sample holder, a cover lid, a heated cover operatively coupled to the cover lid, and a drive assembly for moving the cover lid and the heated cover. The cover lid is configured to move in a direction toward the sample block from an open position to a closed position. The heated cover is configured to move in a direction toward the sample block from a raised position to a first lowered position, in which the heated cover contacts the sample holder when the sample holder is received by the sample block. The drive assembly includes a motion guide operatively coupled to the cover lid and to the heated cover. The motion guide is configured to move in a direction toward the sample block from a first position, wherein the cover lid is in the open position and the heated cover is in the raised position, to a second position, wherein the cover lid is in the closed position.

In accordance with another embodiment, a thermal cycler system for use with a sample holder configured to receive a plurality of samples includes a sample block configured to receive the sample holder, a heated cover, and a first sensor. The heated cover is configured to move in a direction toward the sample block from a raised position to a first lowered position, wherein the heated cover is in contact with the sample holder when the sample holder is received by the sample block, and from the first lowered position to a second lowered position when the sample holder is removed from the sample block, wherein the heated cover is in contact with the sample block. The first sensor is configured to detect whether the heated cover is in the first lowered position.

Various additional features and advantages of the invention will become more apparent to those of ordinary skill in the art upon review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
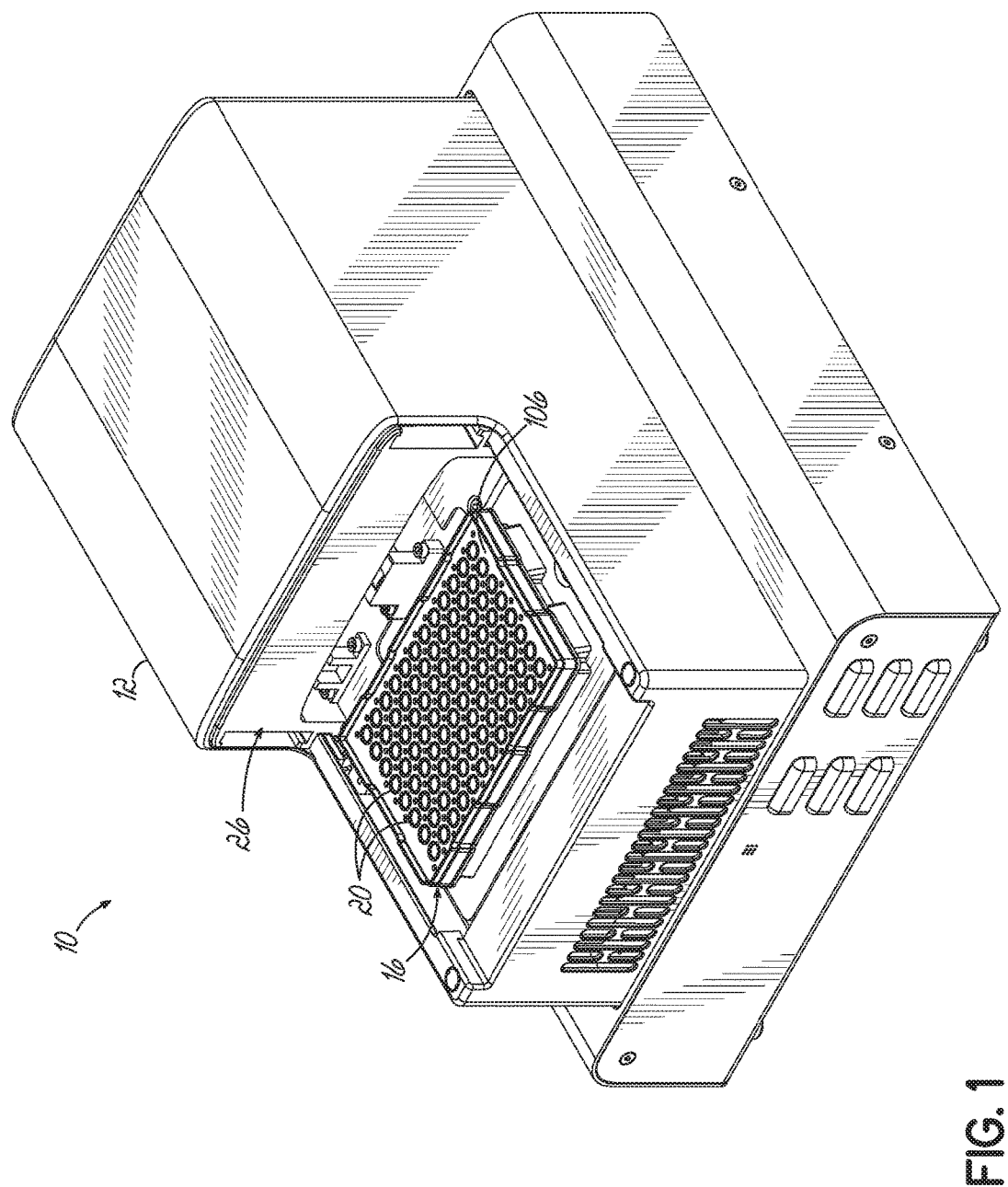
FIG. 1 is a perspective view of a thermal cycler system according to one embodiment showing the cover lid in an open position.
Figure 2:
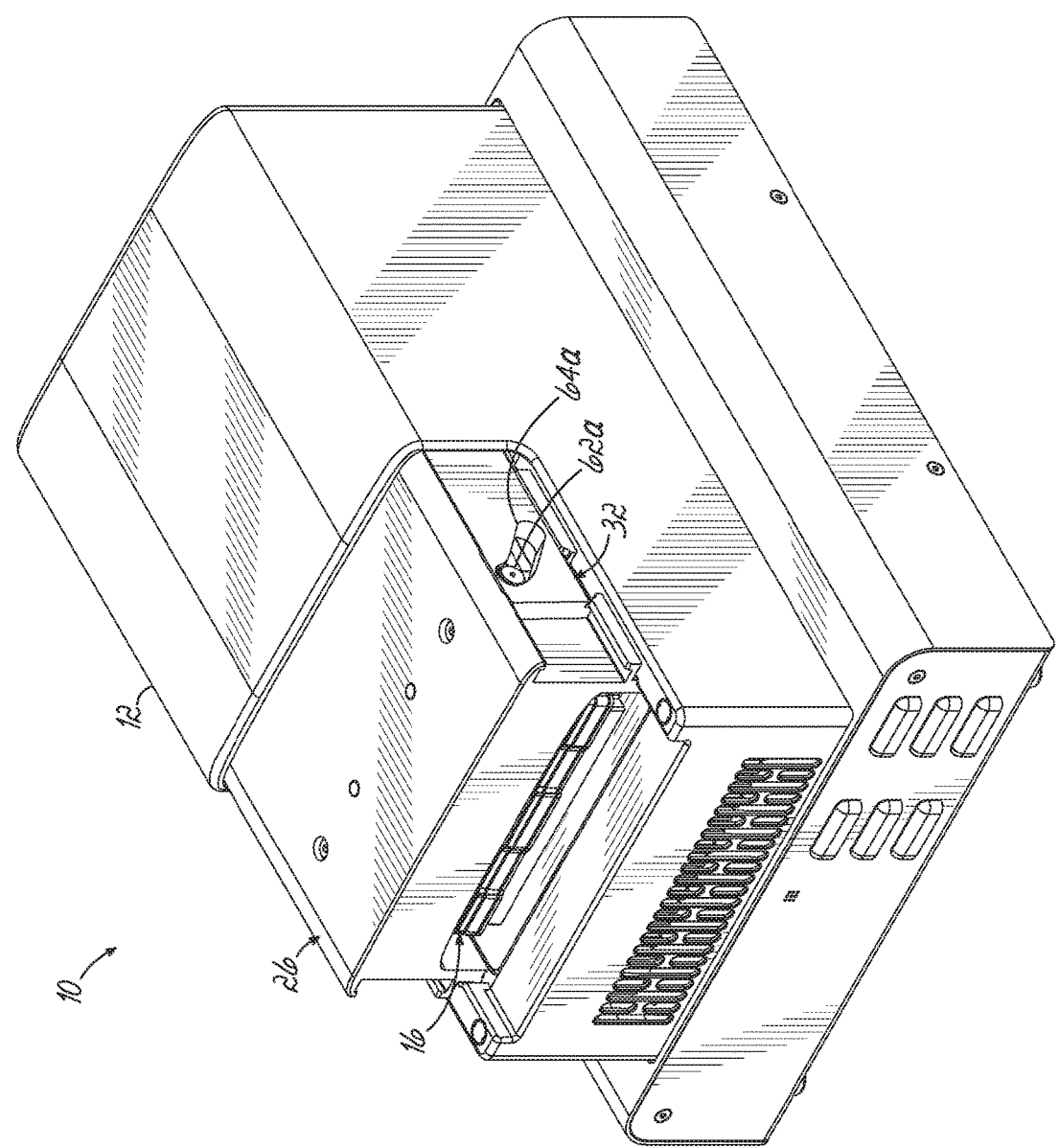
FIG. 2 is a perspective view of the thermal cycler system of FIG. 1 showing the cover lid in a closed position.
Figure 3:
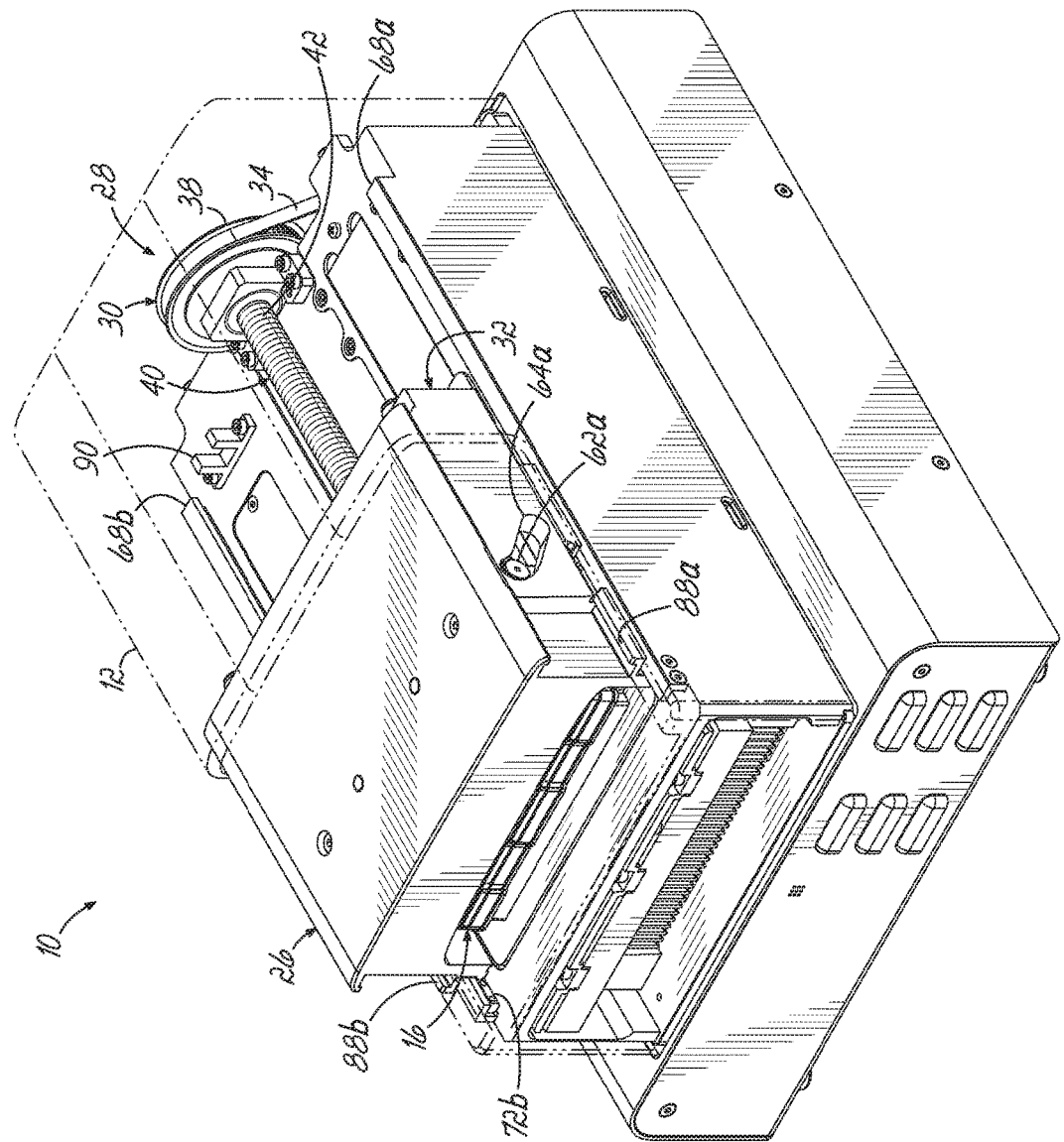
FIG. 3 is a front perspective view of the thermal cycler system of FIG. 1 with an outer housing removed.
Figure 4:
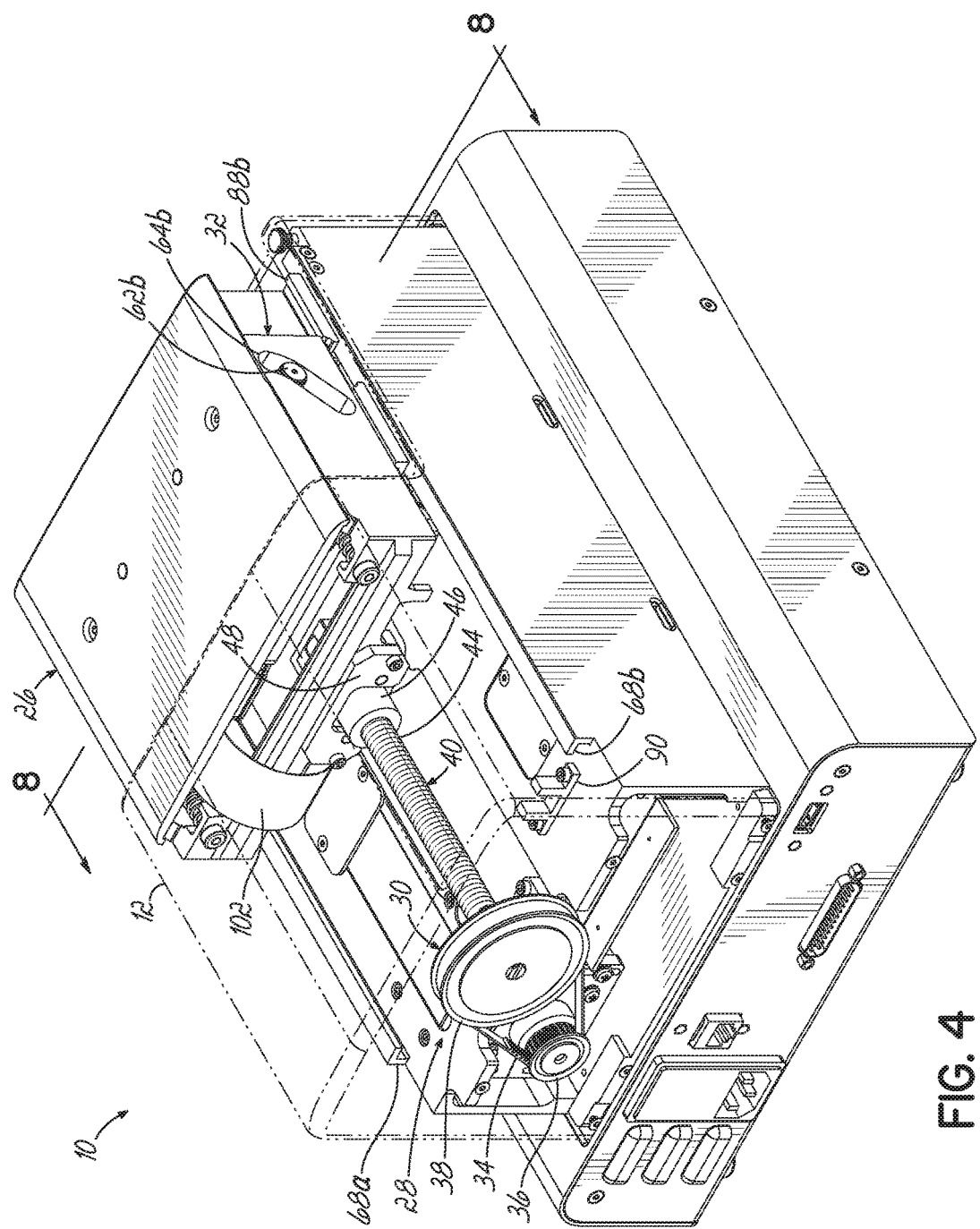
FIG. 4 is a rear perspective view of the thermal cycler system of FIG. 1 with the outer housing removed.

Referring to FIGS. 1-4, a thermal cycler system 10 is shown constructed in accordance with an illustrative embodiment of the present invention. The thermal cycler system 10 includes an outer housing 12 and a sample block 14 configured to receive a sample holder 16. The sample block 14 includes a plurality of cavities 18 and is configured to be loaded with the correspondingly shaped sample holder 16 containing a plurality of biological or biochemical samples located in a plurality of wells 20, as shown best in FIG. 8. The thermal cycler system 10 further includes a heated cover or platen 22 operatively coupled to a pressure bar 24 (shown in FIG. 5A) and a cover lid 26. The heated cover 22 is configured to provide a downward force to the sample holder 16. The downward force provides vertical compression between the sample holder 16, sample block 14, and the other components of a thermal block assembly (not shown), which improves thermal contact between the sample block 14 and the sample holder 16 to heat and cool the samples in the wells 20. As shown in FIGS. 3 and 4, the thermal cycler system 10 also includes a drive assembly 28 for moving the cover lid 26 from an open position (FIG. 1) to a closed position (FIG. 2) and for moving the heated cover 22 from a raised position (FIG. 6A) to a lowered position (FIGS. 6C and 7). The drive assembly 28 includes a belt drive system 30 and a motion guide 32. The thermal cycler system 10 further includes a sensor assembly for sensing various positions of the heated cover 22 and the motion guide 32 as described in greater detail below.

The thermal cycler system 10, unless otherwise indicated, is described herein in the exemplary embodiment using a reference frame in which the sample block 14 is located in the front or forward portion of the thermal cycler system 10, the belt drive system 30 is located in the back or rearward portion of the thermal cycler system 10, and the cover lid 26 is located above the sample block 14 when the cover lid 26 is in the closed position. Consequently, as used herein, terms such as forward, backward, downward, upward, lateral, and vertical used to describe the exemplary thermal cycler system 10 are relative to the chosen reference frame. The embodiments of the present invention, however, are not limited to the chosen reference frame and descriptive terms. For example, the belt drive system 30 may be located in the front or forward portion of the thermal cycler system 10 and be within the scope of the invention. Those of ordinary skill in the art will recognize that the descriptive terms used herein may not directly apply when there is a change in reference frame. Nevertheless, the relative terms used to describe embodiments of the thermal cycler system 10 are to merely provide a clear description of the exemplary embodiments in the drawings. As such, the relative terms forward, backward, downward, upward, lateral, and vertical are in no way limiting the present invention to a particular location or orientation.

With reference to FIGS. 3 and 4, the belt drive system 30 is shown in more detail. The belt drive system 30 is configured to move the motion guide in a lateral direction forward toward the sample block 14 and backward away from the sample block 14. The belt drive system 30 includes a belt 34 looped about a pair of spaced apart pulleys 36, 38 and a screw 40. The belt drive system 30 may also include an electric drive motor and a transmission, such as a gear box, that transfers motive power from the drive motor to the pulley 36 for moving the belt 34 about the pulleys 36, 38. A first end 42 of the screw 40 is coupled to the pulley 38. As the belt 34 rotates around the pulleys 36, 38, the screw 40 rotates. A second end 44 of the screw 40 is operatively coupled to the motion guide 32. More particularly, the second end 44 of the screw 40 extends through a cylindrical tube 46, which is coupled to the motion guide 32 by a bracket 48. The cylindrical tube 46 includes threads (not shown) that cooperate with threads 50 of the screw 40. Thus, as the screw 40 rotates, the engagement of threads 50 with the corresponding threads in the tube 46 provides an axially directed sliding motion of the tube 46 and, thus, the motion guide 32 toward or away from the sample block 14.

Figure 5A:
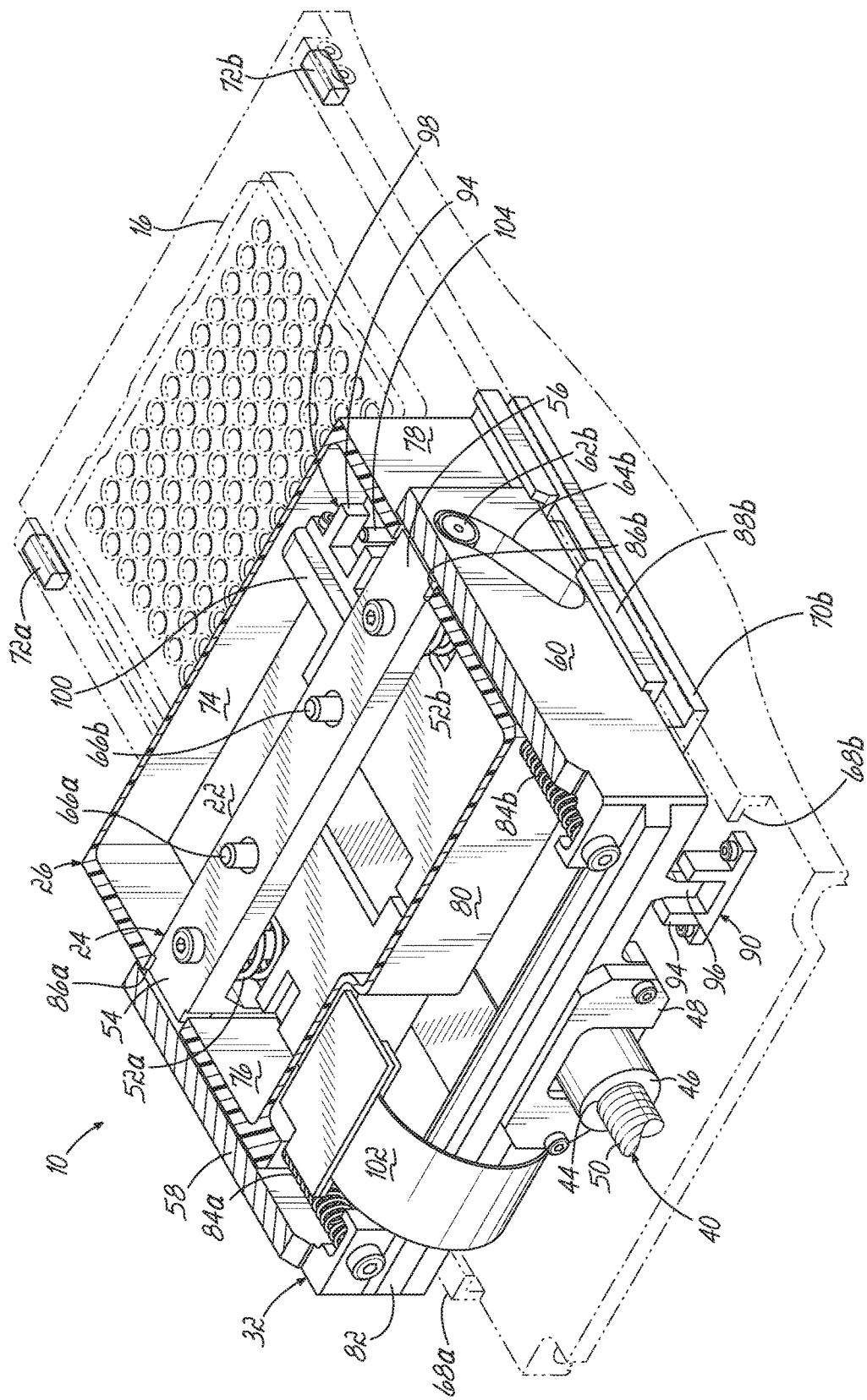
FIGS. 5A-5D are rear perspective views of a portion of the thermal cycler system of FIG. 1 showing a cover lid, a motion guide, and a heated cover in various positions.

With reference to FIG. 5A, the heated cover 22 and the pressure bar 24 are shown in more detail. The heated cover 22 is coupled to the pressure bar 24 via springs 52a, 52b. The springs 52a, 52b may be compression springs or die springs, for example. The dimensions of a die spring may be smaller than a compression spring capable of handling the same load. Die springs may also have a longer service cycle and may be able to withstand high heat. A die spring may be used when higher loads need to be taken or when higher temperatures need to be withstood. In one embodiment, the springs 52a, 52b may be TL16-36 die springs available from Tokyo Hatsujyo Manufacturing Co., Ltd. The pressure bar 24 is engaged with the motion guide 32, and, thus, the heated cover 22 is operatively coupled with the motion guide 32. To that end, ends 54, 56 of the pressure bar 24 include projections 62a, 62b, and side walls 58, 60 of the motion guide 32 include slots 64a, 64b. The projections 62a, 62b extend through the slots 64a, 64b. The slots 64a, 64b are slanted allowing longitudinal motion of the motion guide 32 along a horizontal axis to translate into simultaneous vertical motion of the pressure bar 24 along a vertical axis and, consequently, the heated cover 22. The vertical motion of the pressure bar 24 may be guided by guides 66a, 66b, which are described in greater detail below. When the pressure bar 24 moves in a vertical direction toward the sample block 14, the springs 52a, 52b exert a force on the heated cover 22. Accordingly, the heated cover 22 moves in a vertical direction toward the sample block 14 until it contacts the sample holder 16 when it is received by the sample block 14. When the heated cover 22 is in contact with the sample holder 16, further downward movement is prevented. If the pressure bar 24 continues to move vertically downward, the springs 52a, 52b will compress and the heated cover 22 will exert a force on the sample holder 16.

Referring still to FIG. 5A, the cover lid 26 and the housing 12 are shown in more detail. The housing 12 has shoulders 68a, 68b (shown in phantom) that engage the cover lid 26. More specifically, the cover lid 26 includes ledges 70a, 70b that engage the undersides of the shoulders 68a, 68b, respectively. As the cover lid 26 moves from the opened position to the closed position, the ledges 70a, 70b move along the shoulders 68a, 68b. The underside of the shoulders 68a, 68b includes projections 72a, 72b at an end of the shoulders 68a, 68b. When the cover lid 26 reaches the closed position, the projections 72a, 72b prevent further movement of the cover lid 26 in a direction away from the belt drive system 30.

With further reference to FIG. 5A, the cover lid 26 and the motion guide 32 are shown in more detail. The cover lid 26 includes a front wall 74, opposed side walls 76, 78, and a rear wall 80. The cover lid 26 is configured to be moved longitudinally from the open position to the closed position by the motion guide 32. In the illustrative embodiment, the cover lid 26 and the motion guide 32 are engaged in various manners. To that end, the rear wall 80 of the cover lid 26 is coupled to a cross-bar 82 of the motion guide 32 by springs 84a, 84b. In one embodiment, the springs 84a, 84b may be compression springs, such as type SSC-028-12 coil springs available from Shincoil Spring Pte Ltd. Additionally, the cover lid 26 is engaged with the motion guide 32 via the pressure bar 24. In that regard, the side walls 76, 78 of the cover lid 26 include vertical channels 86a, 86b through which the ends 54, 56 of the pressure bar 24 extend. Thus, when the projections 62a, 62b of the pressure bar 24 move through the slots 64a, 64b of the motion guide 32, the ends 54, 56 of the pressure bar 24 move vertically through the channels 86a, 86b of the cover lid 26. The channels 86a, 86b aid the guides 66a, 66b in preventing relative longitudinal motion between the pressure bar 24 and the cover lid 26. The cover lid 26 further includes troughs 88a, 88b. Each of the troughs 88a, 88b are shown as being discontinuous in the particular embodiment illustrated within FIG. 5A, although the invention is not so limited. The bottoms edges of the side walls 58, 60 of the motion guide 32 are engaged in the troughs 88a, 88b. When the motion guide 32 moves relative to the cover lid 26, the side walls 58, 60 of the motion guide 32 move through the troughs 88a, 88b, respectively.

Figure 5B:
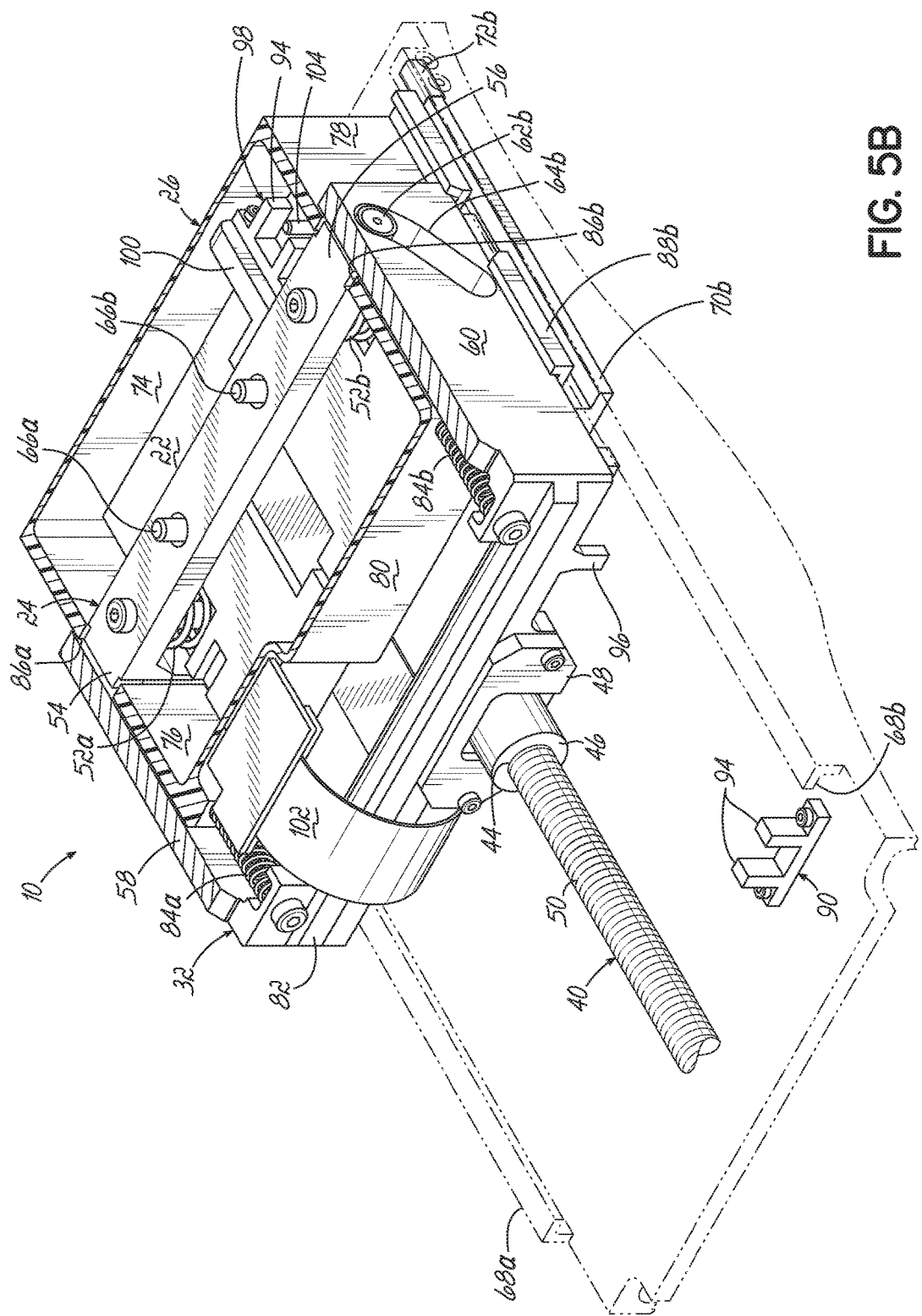

With reference to FIGS. 5A-5D, the operation of the drive assembly 28 is shown in detail. FIGS. 5A and 5B show the movement of the cover lid 26 in a direction toward the sample block 14 from the open position to the closed position. As shown in FIG. 5A, when the motion guide 32 is in a first position, the cover lid 26 is in the open position and the heated cover 22 is in a raised position. When the cover lid 26 is in the open position, the sample holder 16 may be loaded on the sample block 14 by, for example, a robotic arm (not shown). After the sample block 14 receives the sample holder 16, the belt drive system 30 may be engaged. As the belt drive system 30 rotates the screw 40, the motion guide 32 moves in a direction toward the sample holder 16. The forward movement of the motion guide 32 causes the cover lid 26 to move longitudinally in a direction toward the sample holder 16 due at least in part to the engagement between the ends 54, 56 of the pressure bar 24 and the channels 86a, 86b of the cover lid 26. When the cover lid 26 moves forward from the open to the closed position, the cover lid 26 and the motion guide 32 move as one unit. In other words, the relative positions of the cover lid 26 and the motion guide 32 generally remain unchanged. With reference to FIG. 5B, the cover lid 26 is shown in a closed position relative to the sample block 14, and the motion guide 32 is shown in a second position forward of the first position relative to the sample block 14. At this point, further movement of the cover lid 26 in a direction away from the belt drive system 30 is prevented by projections 72a, 72b of the outer housing 12.

Figure 5C:
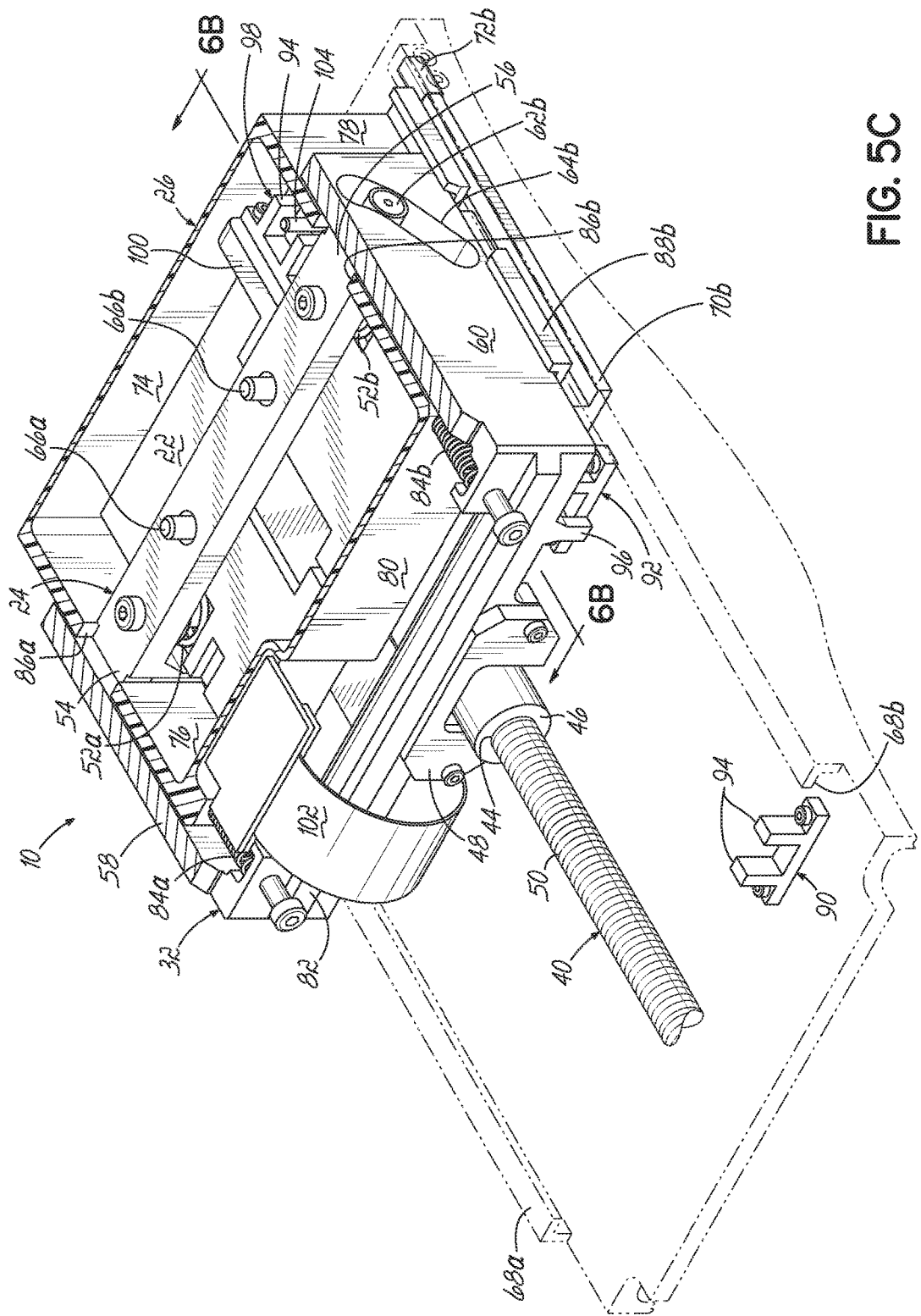
Figure 5D:
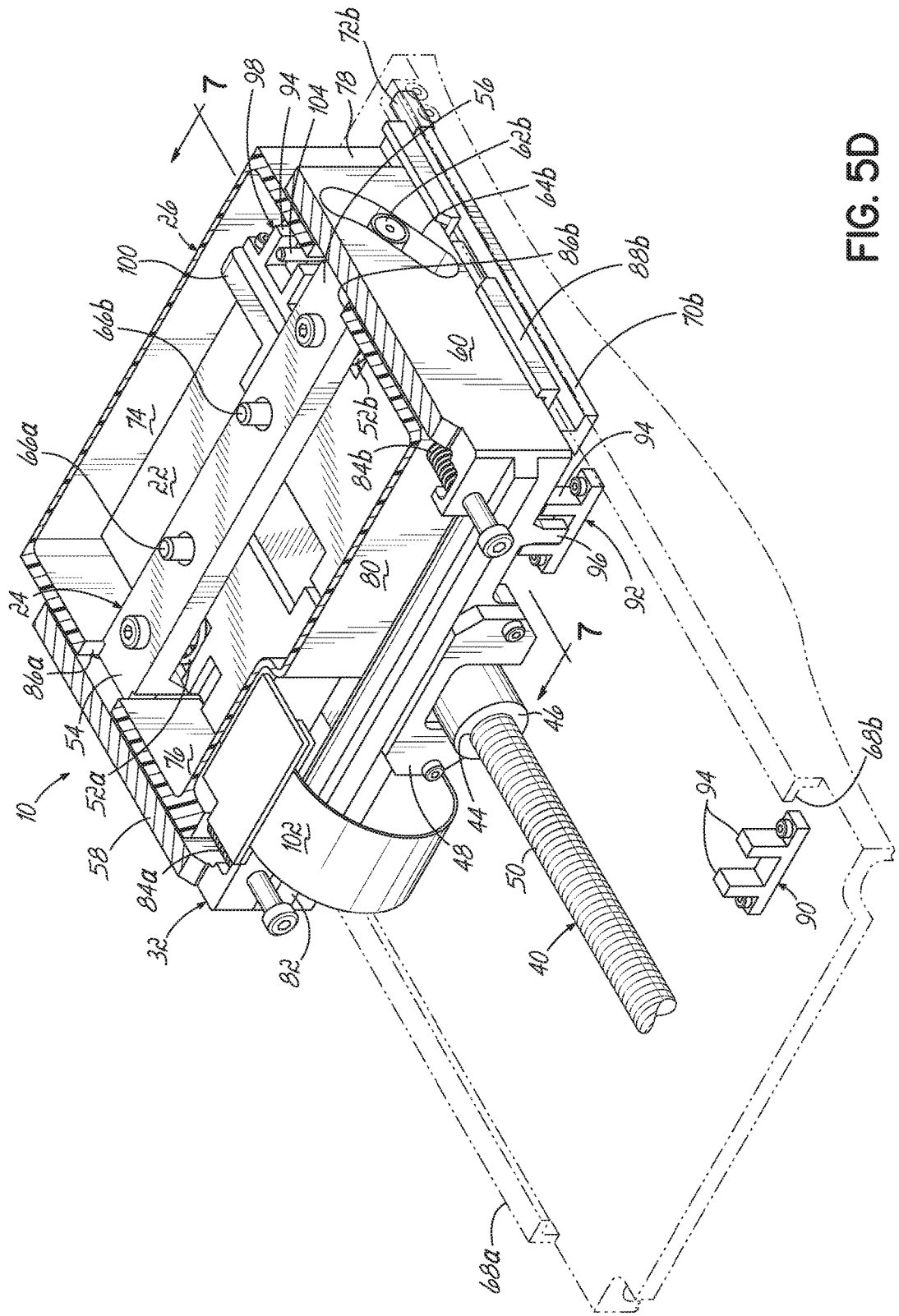

With reference to FIGS. 5C and 5D, the movement of the heated cover 22 and the pressure bar 24 in a direction toward the sample block 14 from the raised position is shown. After the cover lid 26 reaches the closed position and as the screw 40 continues to rotate, the motion guide 32 continues to move in a longitudinal direction toward the sample block 14. Because the cover lid 26 is prevented from moving further forward, the springs 84a, 84b compress as the space between the cross-bar 82 of the motion guide 32 and the rear wall 80 of the cover lid 26 decreases. Accordingly, the side walls 58, 60 and, thus, the slots 64a, 64b of the motion guide 32 move laterally along the side walls 76, 78 of the cover lid 26 of the motion guide 32 in a direction toward the sample block 14. Because the pressure bar 24 is laterally constrained by the channels 86a, 86b of the cover lid 26, the projections 62a, 62b move through the slanted slots 64a, 64b. Additionally, as the motion guide 32 moves relative to the cover lid 26, the side walls 58, 60 of the motion guide 32 move through the troughs 88a, 88b, respectively. In one embodiment, the projections 62a, 62b are rotatable so that, when the pressure bar 24 moves relative to the motion guide 32, the projections 62a, 62b rotate through the slanted slots 64a, 64b. When the projections 62a, 62b move through the slanted slots 64a, 64b, the pressure bar 24 moves in a vertical direction toward the sample block 14. As shown in FIG. 5C, the heated cover 22 moves to a first lowered position in which the heated cover 22 contacts the sample holder 16 when the sample holder 16 is received by the sample block 14. When the heated cover 22 is in the first lowered position, the motion guide 32 is in a third position forward of the second position relative to the sample block 14. As shown in FIG. 5D, when the sample holder 16 is removed from the sample block 14, the heated cover 22 is configured to move to a second lowered position in which the heated cover 22 is in a position intermediate of the first lowered position and the sample block 14. When the heated cover 22 is in the second lowered position, the motion guide 32 is in a fourth position forward of the third position relative to the sample block 14. In the illustrated embodiment, the motion guide 32 will not move to the fourth position when the sample holder 16 is received by the sample block 14.

Referring again to FIGS. 5A-5D, the sensor assembly is shown in detail. The sensor assembly includes a first sensor 90 and a second sensor 92. In one embodiment, the sensors 90, 92 may be deep gap slotted optical switches, such as type OPB820 W sensors available from OPTEK Technology. The exemplary sensors 90, 92 include two spaced apart arms 94 and are configured to detect when a locating pin is positioned between the arms 94. The motion guide 32 includes a locating pin 96. The first sensor 90 is configured to detect if the cover lid 26 is in the open position, as shown in FIG. 5A. To that end, when the cover lid 26 is in the open position, the locating pin 96 of the motion guide 32 is located between the arms 94 of the first sensor 90 so that the sensor 90 detects the presence of the locating pin 96. The second sensor 92 is configured to detect if the cover lid 26 is closed and the sample holder 16 is removed from the sample block 14 (i.e., the motion guide is in the fourth position). In such a case, when the motion guide 32 is in the fourth position, the locating pin 96 is located between the arms 94 of the second sensor 92 so that the second sensor 92 detects the presence of the locating pin 96. When the second sensor 92 detects the presence of the locating pin 96, the drive system may be configured to disengage because the motion guide 32 is in the forward-most position (i.e., the fourth position). As discussed above, if the sample holder 16 is received by the sample block 14, the motion guide 32 will move to the third position but not to the fourth position. Thus, the second sensor 92 will not detect the location of the motion guide 32 if the sample holder 16 is received by the sample block 14 because the locating pin 96 will not be located within the arms 94 of the second sensor 92.

Figure 6A:
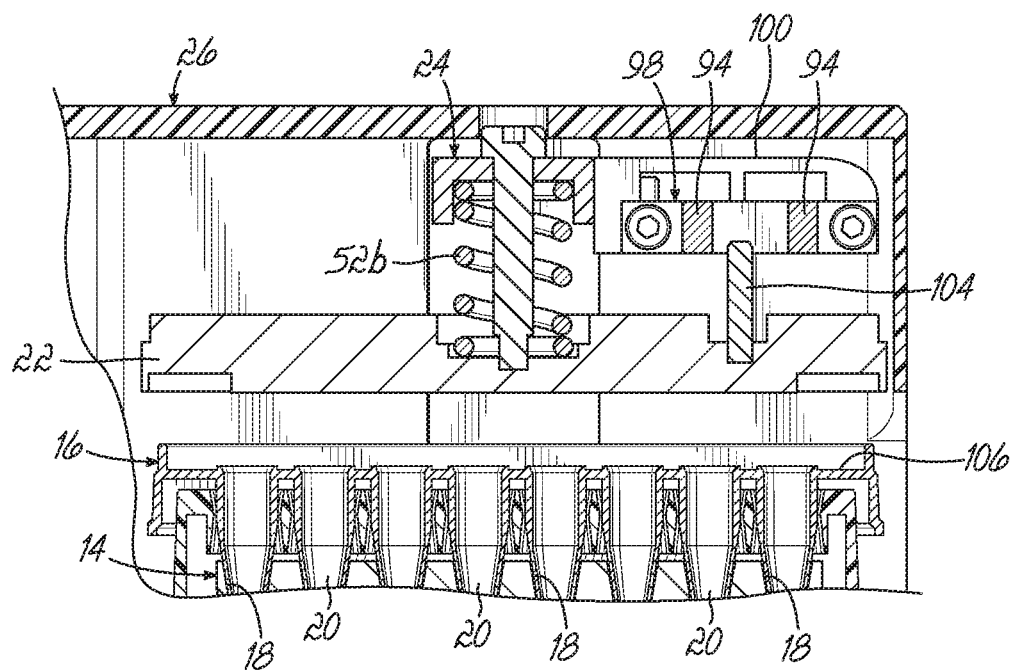
FIGS. 6A-6C are cross-sectional views of a portion of the thermal cycler system taken generally along line 6B-6B of FIG. 5C showing the heated cover in various positions relative to a sample holder positioned on the sample block.
Figure 6B:
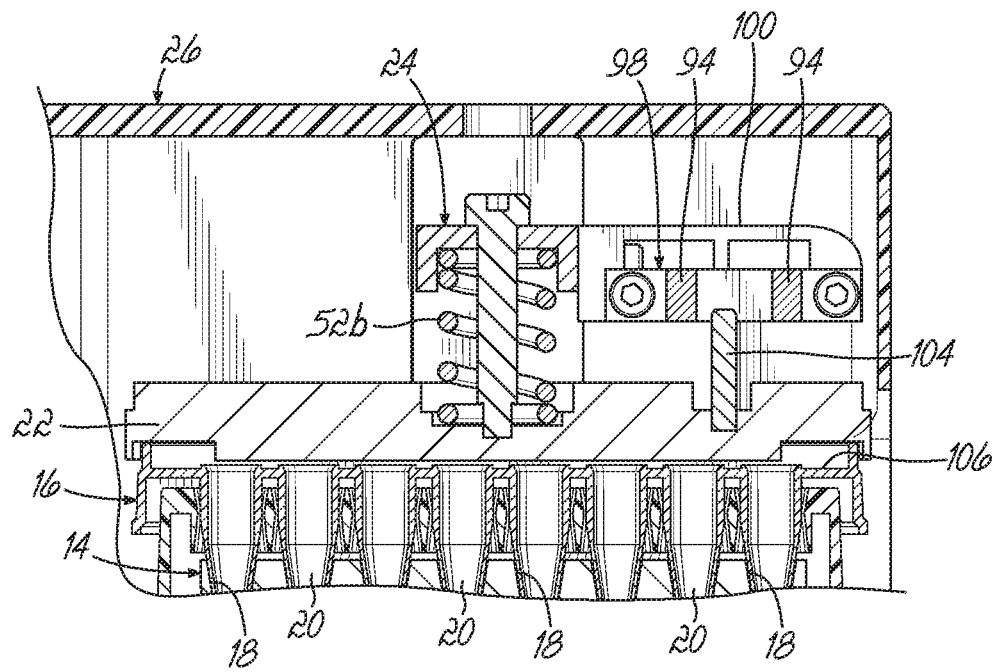
Figure 6C:
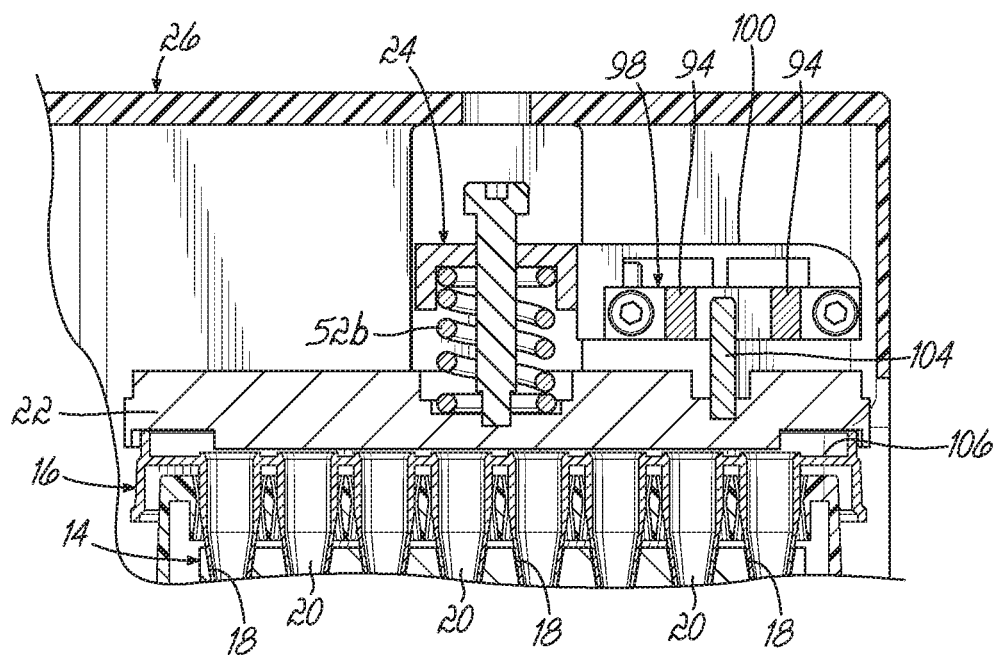
Figure 7:
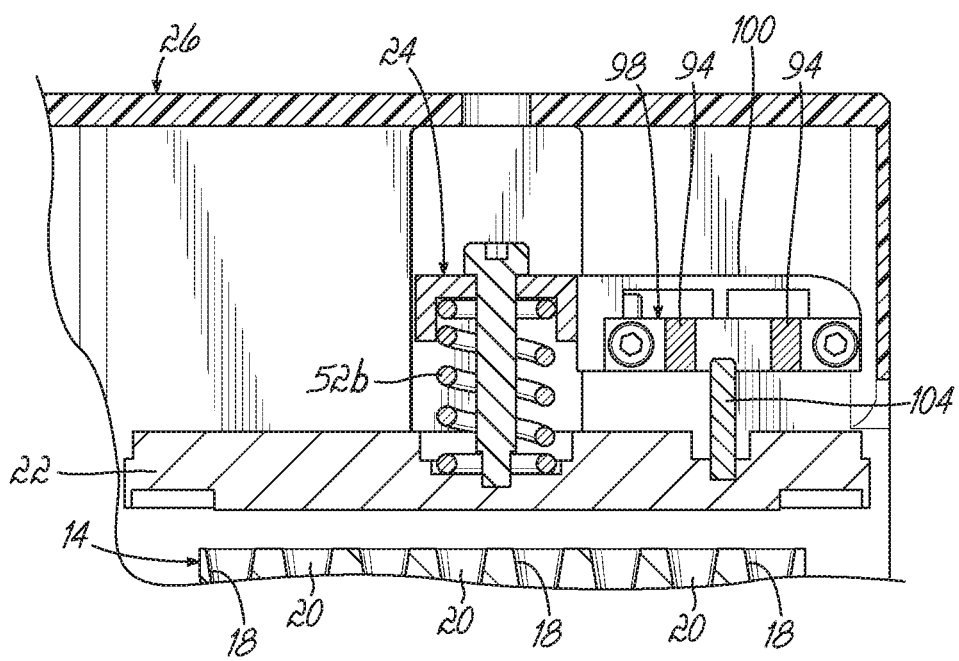
FIG. 7 is a cross-sectional view of a portion of the thermal cycler system taken generally along line 7-7 of FIG. 5D showing the heated cover positioned on the sample block without a sample holder.

With reference to FIGS. 6A-6C and FIG. 7, the movement of the heated cover 22 and the pressure bar 24 is shown in more detail. FIGS. 6A-6C show the movement of the heated cover 22 from a raised position to a first lowered position when the sample holder 16 is received by the sample block 14. In FIG. 6A, the heated cover 22 is shown in the raised position. When the pressure bar 24 moves in a vertical direction towards the sample block 14, the heated cover 22 moves downward to the first lowered position and contacts the sample holder 16, as shown in FIG. 6B. After the heated cover 22 contacts the sample holder 16, the sample holder 16 prevents the heated cover 22 from moving further in a direction toward the sample block 14. Therefore, as shown in FIG. 6C, the springs 52a, 52b begin to compress due to the continued downward movement of the pressure bar 24. In this manner, the heated cover 22 exerts a force on the sample holder 16. In one embodiment, the heated cover 22 may be configured to exert a predetermined force on the sample holder 16. When the predetermined force is reached, the drive assembly 28 may be configured to stop moving the motion guide 32 and, thus, the pressure bar 24, so that the predetermined force is not exceeded. In one embodiment, the heated cover 22 may be configured to exert a force of 96 lbf on the sample holder 16. If the sample holder 16 is removed from the sample block 14, as shown in FIG. 7, the heated cover 22 moves to the second lowered position.

Referring again to FIGS. 6A-6C and FIG. 7, the sensor assembly further includes a third sensor 98 coupled to the pressure bar 24 via an arm 100. The third sensor 98 is configured to detect if the cover lid 26 is in the closed position and the sample holder 16 is received by the sample block 14. More particularly, the third sensor 98 may be configured to detect whether the heated cover 22 is exerting a predetermined force on the sample holder 16. When the third sensor 98 detects that the heated cover 22 is exerting a predetermined force on the sample holder 16, the thermal cycler system 10 may be configured to disengage the drive assembly 28 to prevent exceeding the predetermined force. In the illustrated embodiment, the thermal cycler system 10 includes a flexible connector 102, as illustrated previously in FIGS. 5A-5D. The flexible connector 102 may connect the heated cover 22 and, for example, the third sensor 98. In one embodiment, the flexible connector 102 may also connect to a printed circuit board (not shown). After the heated cover 22 is exerting a predetermined force on the sample holder 16, the thermal cycler system 10 may then proceed to the next step of the PCR process. In the illustrated embodiment, the third sensor 98 is configured to detect a locating pin 104 coupled to the heated cover 22 when the pressure bar 24 and the heated cover 22 are spaced apart by a predetermined distance. The predetermined distance is based on the predetermined force to be exerted on the sample holder 16 and depends at least in part on the characteristics of the springs 52a, 52b. In that regard, the compressed length of the springs 52a, 52b depends on the pressure bar 24 and the force being exerted by the heated cover 22. Therefore, the distance between the pressure bar 24 and the heated cover 22 when the predetermined force is being exerted on the sample holder 16 may be determined based on the characteristics of the springs 52a, 52b. Accordingly, when the heated cover 22 is exerting the predetermined force on the sample holder 16, the locating pin 104 is located within the arms 94 of the third sensor 98 so that the sensor 92 detects the presence of the locating pin 96. Consequently, as shown in FIG. 7, the pressure bar 24 and the heated cover 22 will be spaced apart by a distance greater than the predetermined distance and the locating pin 96 is not located between the arms 94 such that the third sensor 98 will not detect the presence of the locating pin 96. Therefore, the third sensor 98 does not detect when the heated cover 22 is in the second lowered position. At this point, however, the second sensor 92 will detect that the motion guide 32 is in the fourth position and the drive assembly 28 may be disengaged.

Advantageously, the configuration of the sensor assembly allows for the thermal cycler system 10 to be compatible with sample holders 16 that vary in design, such as the design of a deck 106 of the sample holder 16. For example, the deck thickness of commercially available sample holders varies. Accordingly, when the heated cover 22 is in the first lowered position, the distance of the heated cover 22 from the sample block 14 may vary depending on the thickness of the particular sample holder 16. However, the thickness of the deck 106 does not affect the detection of the presence of the sample holder 16 because the third sensor 98 indirectly detects the presence of the sample holder 16 based on the predetermined force. Thus, the heated cover 22 may be configured to exert the same predetermined force on sample holders 16 having varying deck thicknesses.

Figure 8:
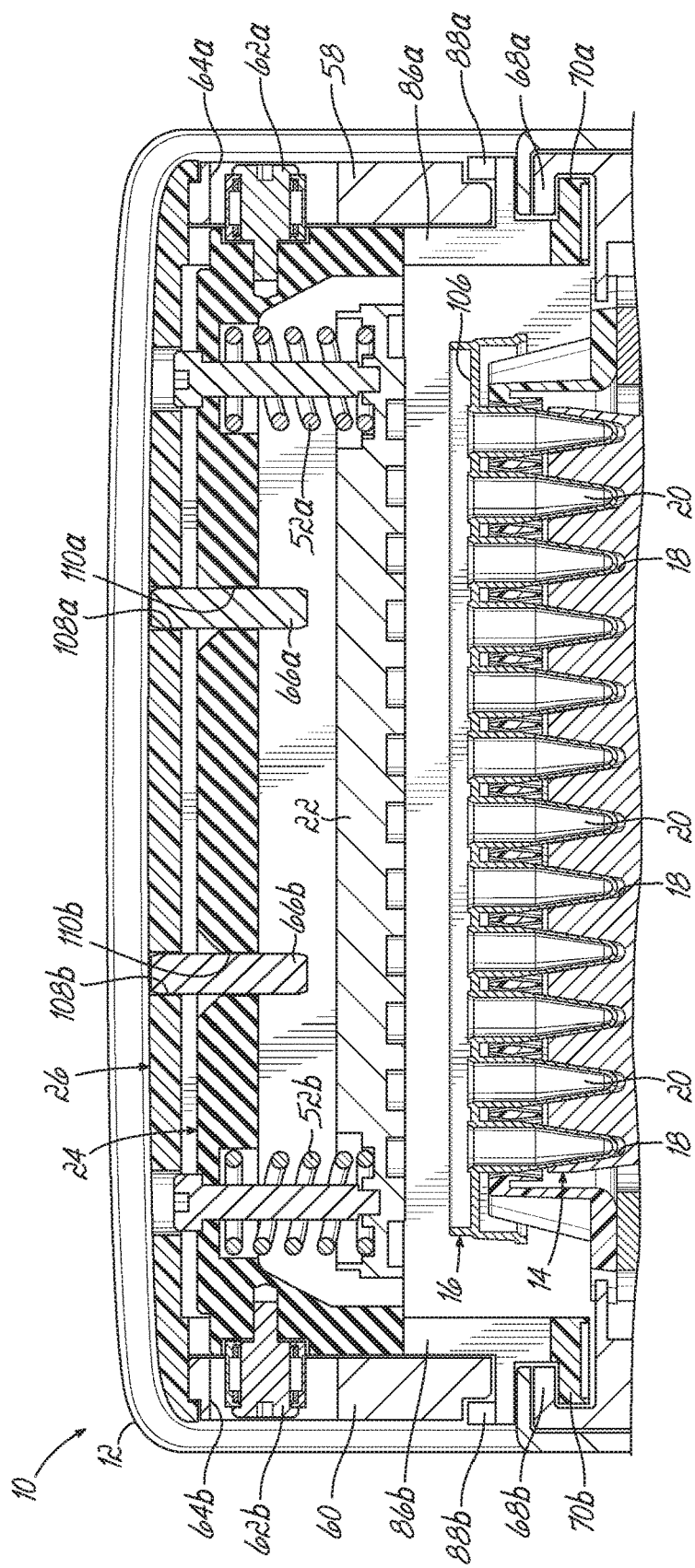
FIG. 8 is a cross-sectional view of a portion of the thermal cycler system taken generally along line 8-8 of FIG. 4 showing the guides.

With reference to FIG. 8, the guides 66a, 66b are shown in more detail. The guides 66a, 66b are coupled to the cover lid 26. More particularly, the guides 66a, 66b are secured in bores 108a, 108b of the cover lid 26. The guides 66a, 66b extend from the cover lid 26 in a direction toward the sample block 14 and into through-holes 110a, 110b in the pressure bar 24. The guides 66a, 66b are slidable through the through-holes 110a, 110b. Thus, as the pressure bar 24 moves in a direction toward the sample block 14, the through-holes 110a, 110b slide in a downward direction along the guides 66a, 66b. The guides 66a, 66b aid in preventing horizontal or lateral movement of the pressure bar 24 and, thus, the heated cover 22. Advantageously, preventing horizontal or lateral movement of the heated cover 22 reduces potential shear stress on the sample holder 16 that results from the heated cover 22 being lowered at an angle towards the sample holder 16.

Still referring to FIG. 8, the sample block 14 and the sample holder 16 are shown in more detail. As discussed above, in various embodiments, the sample block 14 may have a plurality of cavities 18 configured to receive a plurality of correspondingly shaped wells 20 of the sample holder 16. The wells 20 are configured to receive a plurality of samples, wherein the wells 20 may be sealed within the sample holder 16 via a lid, cap, sealing film or other sealing mechanism between the wells 20 and the heated cover. In the illustrative embodiment, there are 96 cavities 18 in the sample block 14. In such an embodiment, the sample holder 16 may be a 96-well microtiter plate. It should be recognized that the sample block 14 and the sample holder 16 may have alternate configurations. For example, the sample holder 16 may be, but is not limited to, any size multi-well plate, card or array including, but not limited to, a 32-well microtiter plate, a 50-well microtiter plate, a 384-well microtiter plate, a 484-well microtiter plate, a microcard, a through-hole array, or a substantially planar holder, such as a glass or plastic slide. The wells 20 in various embodiments of a sample holder 16 may include depressions, indentations, ridges, and combinations thereof, patterned in regular or irregular arrays formed on the surface of the sample holder 16. Sample or reaction volumes can also be located within wells or indentations formed in a substrate, spots of solution distributed on the surface a substrate, or other types of reaction chambers or formats, such as samples or solutions located within test sites or volumes of a microfluidic system, or within or on small beads or spheres. Samples held within the wells 20 may include one or more of at least one target nucleic acid sequence, at least one primer, at least one buffer, at least one nucleotide, at least one enzyme, at least one detergent, at least one blocking agent, or at least one dye, marker, and/or probe suitable for detecting a target or reference nucleic acid sequence.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A thermal cycler system for use with a sample holder configured to receive a plurality of samples, the system comprising:
a sample block configured to receive the sample holder at a surface of the sample block, a longitudinal direction being defined perpendicular to a normal of the surface;
a cover lid configured to move along the longitudinal direction toward the sample block from an open position distal the sample block until reaching a closed position proximal and above the sample block;
a cover operatively coupled to the cover lid, the cover configured to be heated and to move in a direction, perpendicular to the longitudinal direction, toward the sample block from a raised position to a lowered position, in which the cover contacts the sample holder when the sample holder is in the sample block and the cover lid is in the closed position; and
a drive assembly for moving the cover lid and the cover, the drive assembly including a motion guide operatively coupled and movable relative to the cover lid and to the cover, the motion guide being configured to move in the longitudinal direction and with the cover lid from the open position to the closed position, and the motion guide being configured to move in the longitudinal direction and relative to the cover lid upon the cover lid being in the closed position.

2. The thermal cycler system of claim 1, wherein the cover lid and the motion guide are coupled by at least one spring, the at least one spring being configured to compress in the longitudinal direction when the motion guide continues to move in the longitudinal direction after the cover lid reaches the closed position.

3. The thermal cycler system of claim 2, wherein the cover lid comprises a rear wall, the motion guide comprises a crossbar, and the at least one spring extends between the rear wall and the crossbar.

4. The thermal cycler system of claim 1, wherein the motion guide comprises a slot, the system further comprising:
a pressure bar coupled to the cover, the pressure bar comprising a bar end and a projection from the bar end configured to extend through the slot,
wherein the projection is configured to move through the slot in the direction perpendicular to the longitudinal direction when the motion guide continues to move in the longitudinal direction after the cover lid reaches the closed position.

5. The thermal cycler system of claim 4, wherein the cover lid comprises a channel extending in the direction perpendicular to the longitudinal direction and configured to receive the bar end and minimize longitudinal movement of the pressure bar.

6. The thermal cycler system of claim 5, wherein the channel is a first channel, the bar end is a first bar end, the cover lid comprises a second channel opposite the first channel, the second channel configured to receive the second bar end and minimize the longitudinal movement of the pressure bar.

7. The thermal cycler system of claim 4, wherein the slot is a first slot and the motion guide comprises a second slot opposite the first slot, the bar end is a first bar end and the pressure bar comprises a second bar end opposite the first bar end, the projection is a first projection and the pressure bar comprises a second projection from the second bar end configured to extend through the second slot.

8. The thermal cycler system of claim 4, wherein:
the pressure bar comprises at least one through-hole extending in the direction perpendicular to the longitudinal direction; and
the cover lid comprises at least one guide extending through the at least one through-hole configured to guide movement of the cover in the direction perpendicular to the longitudinal direction from the raised position to the lowered position and minimize the longitudinal movement of the pressure bar in the longitudinal direction.

9. The thermal cycler system of claim 4, further comprising a first sensor configured to detect whether the cover lid is in the open position.

10. The thermal cycler system of claim 9, further comprising a second sensor configured to detect whether the cover lid is in the closed position.

11. The thermal cycler system of claim 10, wherein the motion guide comprises a locating pin, the first sensor comprises a first pair of arms configured to receive the locating pin, the second sensor comprises a second pair of arms configured to receive the locating pin, the first sensor is configured to be activated when the locating pin is received by the first pair of arms, and the second sensor is configured to be activated when the locating pin is received by the second pair of arms.

12. The thermal cycler system of claim 11, further comprising a third sensor configured to detect a pressure exerted by the cover on the sample holder.

13. The thermal cycler of claim 12, wherein the third sensor is coupled to the pressure bar.

14. The thermal cycler of claim 12, wherein the cover comprises a locating pin, the third sensor comprises a pair of arms configured to receive the locating pin, the third sensor is configured to detect the locating pin when the locating pin is received by the pair of arms, and the detection corresponds to a predetermined pressure exerted by the cover on the sample holder, a predetermined distance between the pressure bar and the cover, or both.

15. The thermal cycler of claim 12, wherein the third sensor is further configured to detect if the cover lid is in the closed position, the sample holder is in the sample block, or both.

16. The thermal cycler system of claim 4, wherein the pressure bar is coupled to the cover via at least one spring.

17. The thermal cycler system of claim 16, wherein the at least one spring comprises a compression spring, a die spring, or both.

18. The thermal cycler system of claim 1, wherein the drive assembly includes a belt drive system.

19. The thermal cycler system of claim 1, further comprising a housing configured to enclose the cover lid when the cover lid is in the open position.

20. The thermal cycler system of claim 19, wherein the housing comprises at least one projection configured to prevent continued movement of the cover lid in the longitudinal direction after reaching the closed position.

21. The thermal cycler system of claim 1, further comprising the sample holder.

22. The thermal cycler system of claim 21, wherein the sample holder comprises a microtiter plate, a multi-well plate, a card, a through-hold array, or a substantially planar holder, or any combination thereof.

23. The thermal cycler system of claim 1, wherein the cover lid is at least partially inside the motion guide.

24. The thermal cycler system of claim 1, wherein the motion guide comprises at least one sidewall and the cover lid comprise at least one trough configured to receive the at least one sidewall and permit motion of the motion guide relative to the cover lid.

\* \* \* \* \*